United States Patent [19]
Fournier et al.

[11] Patent Number: 5,989,911
[45] Date of Patent: Nov. 23, 1999

[54] SITE-SPECIFIC SYNTHESIS OF PSEUDOURIDINE IN RNA

[75] Inventors: Maurille J. Fournier; Jingwei Ni, both of Amherst, Mass.

[73] Assignee: University of Massachusetts, Boston, Mass.

[21] Appl. No.: 09/075,395

[22] Filed: May 8, 1998

Related U.S. Application Data

[60] Provisional application No. 60/046,132, May 9, 1997.

[51] Int. Cl.⁶ ............................. C12Q 1/68; C12N 15/81; C12N 15/11; C07H 21/04
[52] U.S. Cl. ............................. 435/375; 435/6; 435/91.1; 435/254.2; 435/320.1; 536/23.1; 536/24.1; 536/24.32; 536/24.5
[58] Field of Search .......................... 435/6, 91.1, 91.31, 435/325, 375, 243, 254.2, 320.1; 536/23.1, 24.1, 24.3, 24.33, 24.5

[56] References Cited

PUBLICATIONS

Balakin, et al., "The RNA World of the Nucleolus: Two Major Families of Small RNAs Defined by Different Box Elements with Related Functions," *Cell*, vol. 86:823–834, (1996).
Caffarelli, et al., "Processing of the intron–encoded U16 and U18 snoRNAs: The conserved C and D boxes control both the processing reaction and the . . . ," *The EMBO Journal*, vol. 15:1121–1131 (1996).
Tsui, et al., "Absence of hisT–Mediated tRNA Pseudouridylation Results in a Uracil Requirement That Interferes with *Escherichia coli* K–12 Cell Division," *Journal of Bacteriology*, vol. 173:7395–7400 (1991).
Ganot, et al., "The family of box ACA small nucleolar RNAs is defined by an evolutionarily conserved secondary structure and ubiquitous sequence . . . ," *Genes & Development*, vol. 11:941–956 (1997).
Hagervall, et al., "Role of tRNA modification in translational fidelity," *Biochimica et Biophysica Acta*, vol. 1050:263–266 (1990).
Hartshorne, et al., "A common core structure for U3 small nucleolar RNAs," *Nucleic Acids Research*, vol. 22:3354–3364 (1994).
Huang, et al., "Accumulation of U14 Small Nuclear RNA in *Saccharomyces cerevisiae* Requires Box C, Box D, and a 5',3' Terminal Stem," *Molecular and Cellular Biology*, vol. 12:4456–4463 (1992).
Jarmolowski, et al., "Identification of essential elements in U14 RNA of *Saccharomyces cerevisiae*," *The EMBO Journal*, vol. 9:4503–4509 (1990).

Kiss–Laszlo, et al., "Site–Specific Sugar Methylation of rRNA: A Novel Function for Small Nuclear RNAs," RNA 1996, The First Annual Meeting of the RNA Society, Abstract (1996).
Kiss–Laszlo, et al., "Site–Specific Ribose Methylation of Preribosomal RNA: A Novel Function for Small Nucleolar RNAs," *Cell*, vol. 85:1077–1088 (1996).
Tyc, et al., "U3, U8 and U13 comprise a new class of mammalian snRNPs localized in the cell nucleolus," *The EMBO Journal*, vol. 8:3113–3119 (1989).
Watkins, et al., "Elements essential for processing intronic U14 snoRNA are located at the termini of the mature snoRNA sequence and include conserved nucleotide boxes C and D," *RNA*, vol. 2:118–133 (1996).
Xia, et al., "Identification of specific nucleotide sequences and structural elements required for intronic U14 snoRNA processing," *RNA*, vol. 3:17–26 (1997).
Maden et al, Database Biosis on STN, "Eukaryotic ribosomal RNA: The recent excitement in the nucleotide modification problem," Abstract No. 99655451, *Chromosoma*, vol. 105:391–400, (1997).
Ni et al, "Small Nucleolar RNAs Direct Site–Specific Synthesis of Pseudouridine in Ribosomal RNA," *Cell*, vol. 89:565–573 (1997).
Peculis, "RNA Processing: Pocket Guides to Ribosomal RNA," *Current Biology*, vol. 7:R480–R482 (1997).
Tollervey et al, "Function and Synthesis of Small Nucleolar RNAs," *Current Opinion in Cellular Biology*, vol. 9:337–342 (1997).
International Search Report dated Jul. 6, 1998.

*Primary Examiner*—John L. LeGuyader
*Assistant Examiner*—Mark L. Shibuya
*Attorney, Agent, or Firm*—Fish & Richardson P.C.

[57] ABSTRACT

The invention features a modified small nucleolar ribonucleic acid (snoRNA) that directs the conversion of a uridine to a pseudouridine in a target nucleic acid, e.g., RNA, that includes first and second flanking regions located on either side of the uridine. The modified snoRNA includes a ribonucleotide sequence of a box H/ACA snoRNA including a Domain A sequence and a Domain B sequence, or a Domain A sequence and a Domain C sequence, wherein the snoRNA is modified in that the Domain A sequence is replaced by a first recognition sequence complementary to at least three consecutive nucleotides in the first flanking region in the target nucleic acid, and the Domain B or C sequence is replaced by a second recognition sequence complementary to at least three consecutive nucleotides in the second flanking region in the target nucleic acid.

32 Claims, 8 Drawing Sheets

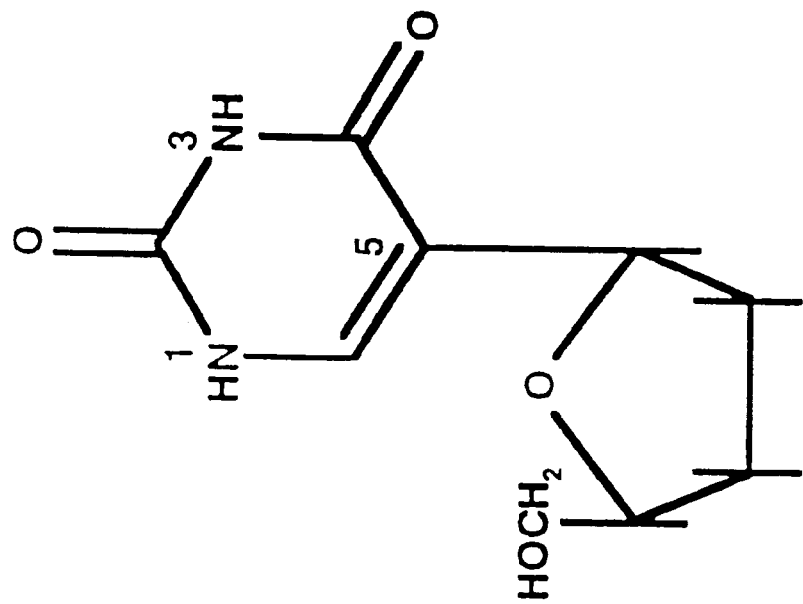
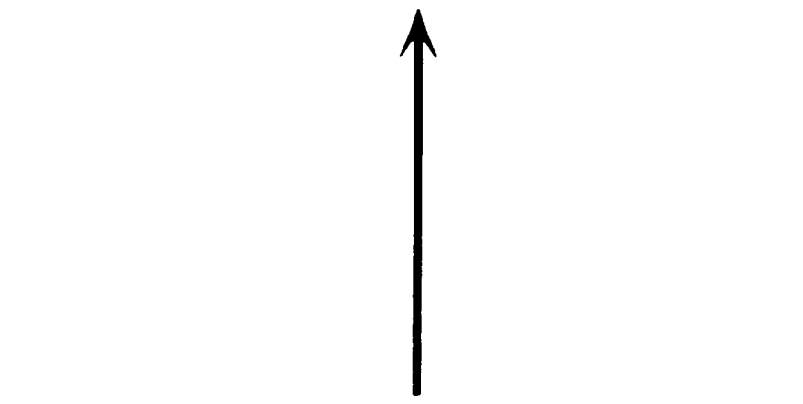
FIG. 1

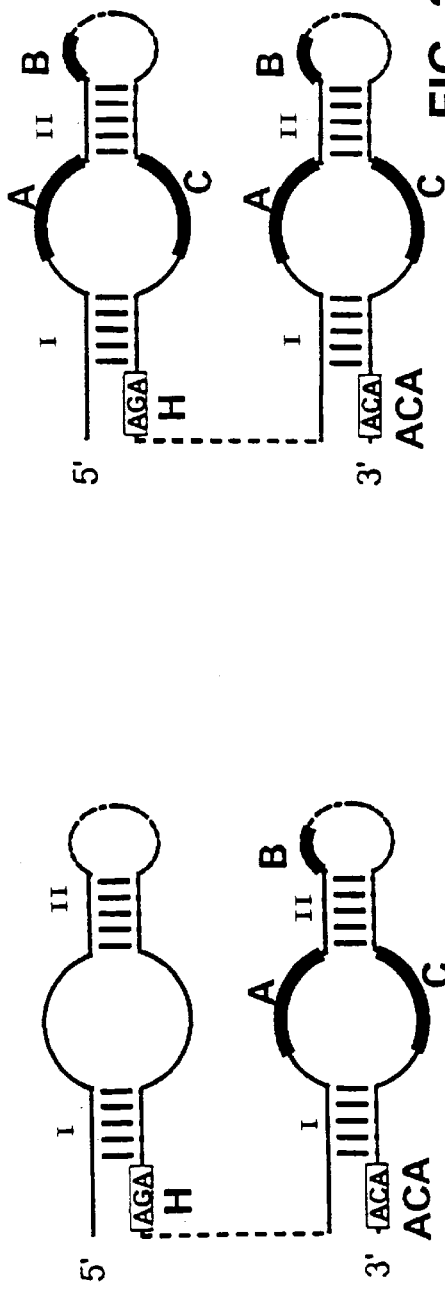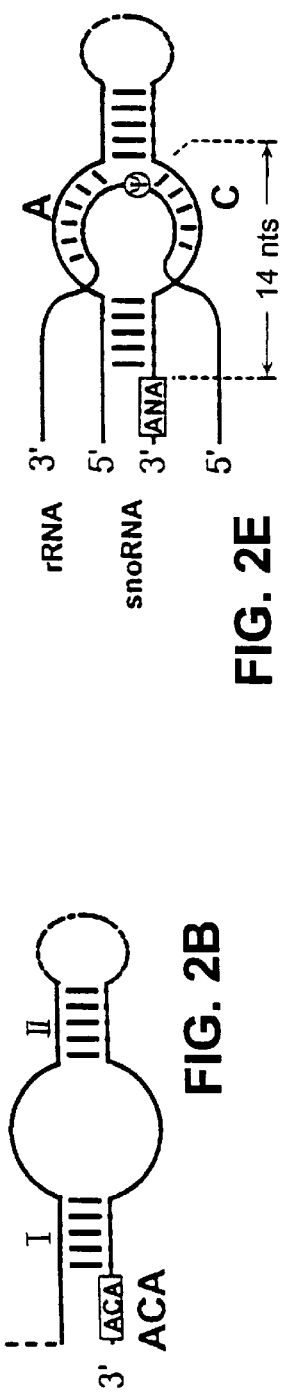

```
                2263
                 |
LSU rRNA   3'---GUAAACCGAUGGAUUCUCψCAGUAUCAAUGAGGGGCAAA---5' (SEQ ID NO:21)
                 ||||||       |0||0|||||||
           5'---CCGGGUCAUUUAUAAGAACUGAGUGGAUUGCUAGUUGUUU      (SEQ ID NO:22)
                                         ||||| |||||||
snR3       3'---AUAUCAGUAGAAGACUGUGAGCUCAGAGUAAGUCGAUUAGU 985                959
                     |                  |
LSU rRNA   3'---UUAGUAAGCGAAAUGGAGUAUUUψUGACUAUGCUCGAAGACGAUAGGACψCCCUUGA---5' (SEQ ID NO:23)
                    ||||||              ||||| ||||||||
           5'---ACACUCAUGAGCGUCCUCAUAUCUGGGC-GCUUCUCACAGGUGCUUC         (SEQ ID NO:24)
                        ||||00|||  |||| ||||||
snR8       3'---AUAGAGUAGCGCGUC—GAUGGCUAGACCCGGUUACCCUCUGUGAUUUU

2919
                     |
LSU rRNA   3'---UACAAGGGAUAAAUCACCCACUψGUUUAGGUUGCGAAUGGCUUA---5' (SEQ ID NO:25)
                    |||||              ||||| |||||
           5'---AAAUUUAUCGAUCUUGGGGUGCAACAGUCUUU---CUGUCGUCGUUUUUAGCAGAUCU (SEQ ID NO:26)
                        ||||||||   |||||| |||||
snR10      3'---ACAUAAUAGUUAGGA---ACGUUGCCAGGAGUAGGCCCGUGUGCUUCCAUUGGGAA
```

FIG. 6A

```
SSU rRNA    3'----UCUGAUGCUGCCAUAGACΨAGUAGAAGCUAGGGGAUGAAA---5'   (SEQ ID NO:27)
                              |||||        |||||||    |||o||oo|
snR31       5'----AUUAGAAAGAUGUAAUCUCCAGCUGU-UGAUAUUAGAGGGGAAGCCUUCUC
                              |||o||        |||||||        |||||||||| (SEQ ID NO:28)
            3'----ACAUCUUGCUUAGUACUGGUUGACAUAGUCCACAAAUUUUCCGUCCACUUU
                                    1000

LSU rRNA    3'----AAACUGUAAGUCUCGUGACCCGUCΨUAGUGUAACGCAGUUGUA---5'   (SEQ ID NO:29)
                              ||||||        ||||||||
snR32       5'----GAUAGAUUGAACGUUGCUGGGGCGCCUGGUGUUGAUCAUUUC
                              |||||        ||||||||||  (SEQ ID NO:30)
            3'----ACAUCUAUGUGAC--------UAAGGUUAUAGAGUAAAGU
                                    2190

LSU rRNA    3'----UGUAUAAAUUUCAAACUCΨAUCCAGUCCAGUAAAGC---5'   (SEQ ID NO:31)
                              |||||        ||||||||
snR33       5'----CUUUACACCGGUUUGAGUCGGUUCCU----UCGUUUU
                              |||||        ||||||||  (SEQ ID NO:32)
            3'----ACAGGUGUGUGAAGAUAUAGUAAGGUUGAUUC
                                    1041
```

FIG. 6B

```
                    2876
                     |
LSU rRNA    3'- - - GAAGCCAUACUAUCCUUCψCGGCUGUAGCUUCUUAGUU- - -5' (SEQ ID NO:33)
                       |o||||||          |||
            5'- - -UUUGGACAGGAAGUCCGAUUUCUGUGUUCUCA
                   |||||  ooo|   ||o|||  | |||||              (SEQ ID NO:34)
snR34       3'- - -ACAUCUGAAAGAAGCUGAGGGUUAAGAUAGCGGAGCAA 2971
                     |
LSU rRNA    3'- - - GUAGUCAUCCCAUUUUGAψUGGACAGAGUGCUGCCA- - -5' (SEQ ID NO:35)
                    |||||  ||||       ||||o|||
            5'- - -UAAUCCAUCUUUAAAACCAUCGCCGUUAGAGGUUGCUUCUGAGAUU
                   |||||  |||o|    ||||||||||                    (SEQ ID NO:36)
snR42       3'- - -ACAAGGUAUGGAGUCCAGUAGUGGUAAAGUACCCAGCGAAUUGGCU
```

FIG. 6C

SITE-SPECIFIC SYNTHESIS OF PSEUDOURIDINE IN RNA

CROSS REFERENCE TO RELATED APPLICATION

Under 35 USC 119(e)(1), this application claims the benefit of prior U.S. provisional application Ser. No. 60/046,132, filed May 9, 1997 and incorporated herein by reference in its entirety.

STATEMENT AS TO FEDERALLY SPONSORED RESEARCH

The invention was funded in part by National Institutes of Health Grant No. GM 19351. The government may have certain rights in the invention.

FIELD OF THE INVENTION

The invention relates to site-specific synthesis of pseudouridine in ribonucleic acids ("RNA"s). This process is known as pseudouridylation.

BACKGROUND OF THE INVENTION

Two recent advances have altered the understanding of the small nucleolar RNAs ("snoRNA"s) in eukaryotic cells. The first was the discovery that nearly all snoRNAs can be classified into two large families, based on short conserved sequence elements (Balakin et al., *Cell*, 86:823–834, 1996). The families are known as the box C/D and box ACA families. Only one known snoRNA does not belong to either family. This is the phylogenetically conserved MRP/7-2 snoRNA, which is part of a snoRNP complex involved in rRNA processing (Maxwell et al., *Annu. Rev. Biochem.*, 35:897–934, 1995).

Members of the box C/D family contain box C and box D elements that are almost always near the 5' and 3' ends of the snoRNA molecule. These elements have been implicated the synthesis, localization, and function of snoRNAs (see, e.g., Maxwell et al., supra; and Huang et al., *Mol. Cell. Biol.*, 12:4456–4463, 1992).

The box ACA family includes snoRNAs with an ACA triplet (or certain active variants thereof) located three nucleotides upstream from the 3' terminus (Balakin et al., *Cell*, 86:823–834, 1996). These snoRNAs are also referred to as "ACA snoRNAs" or "ACA box snoRNAs."

SUMMARY OF THE INVENTION

The invention is based on the discovery that pseudouridylation, a natural process that converts uridine nucleotides in eukaryotic ribosomal RNA ("rRNA") into pseudouridine (or "ψ"), is dependent on the presence of specific ACA box snoRNAs. ACA snoRNAs generally contain a H box at the Hinge region of the secondary structure. Thus, ACA snoRNAs are also termed "box H/ACA snoRNAs," "H/ACA snoRNAs," or "H/ACA box snoRNAs" herein. It has been discovered that: (1) pseudouridine formation is dependent on the presence of an appropriate, targeting or guide H/ACA box snoRNA; (2) pseudouridine synthesis occurs at an rRNA site bordered by one to three sequences complementary to the snoRNA; (3) the snoRNAs and the rRNA sites of modification can be arranged into common structure motifs that correlate snoRNA sequence and secondary structure elements with the rRNA sites of modification; (4) in these common structure motifs, the uridine to be modified is located at a nearly constant distance (about 15 nucleotides) from the conserved ACA box sequence element located at the 3' end of the snoRNA, or from the H box located in a hinge region of the snoRNA; (5) these motifs predict snoRNA species and sites of modification; (6) weakening the complementarity between the snoRNA and the rRNA region of modification reduces or abolishes ψ formation; and (7) moving the ACA box relative to the normal site of rRNA modification reduces pseudouridylation activity of the original target uridine, and/or causes a ψ to be formed at a new position.

The active variants of the ACA box sequence include, but are not limited to, AUA and AAA. H boxes, on the other hand, have a characteristic sequence represented as ANANNA, where N is any nucleotide (Ganot et al., *Genes & Development*, 11:941–956, 1997; Ganot et al., *Cell*, 89:799–809, 1997). Consensus secondary structures (i.e., common motifs) of the H/ACA snoRNAs have similar folded regions near the 5' and 3' ends followed by the H and ACA boxes, respectively.

Accordingly, the invention provides nucleic acid molecules and methods for use in site-specific pseudouridylation of uridine in nucleic acids (e.g., RNA). The methods of the invention can be used to modulate nucleic acid structure and function, especially processes involving sequence-specific recognition of RNA sequences (i.e., interaction of RNA with DNA, other RNAs, or proteins) such as translation.

In one aspect, the invention features a modified small nucleolar ribonucleic acid (snoRNA) that directs the conversion of a uridine to a pseudouridine in a target nucleic acid (e.g., RNA, or a polynucleotide containing both ribonucleotides and deoxyribonucleotides) that includes first and second flanking regions located on either side of the uridine. The modified snoRNA includes a ribonucleotide sequence of a box H/ACA snoRNA including a Domain A sequence and a Domain B sequence, or a Domain A sequence and a Domain C sequence, wherein the box H/ACA snoRNA is modified in that the Domain A sequence is replaced by a first recognition sequence complementary to at least three or four (e.g., five or six) consecutive nucleotides in the first flanking region in the target RNA, and the Domain B or C sequence is replaced by a second recognition sequence complementary to at least three consecutive nucleotides in the second flanking region in the target nucleic acid. Complementarity between Domain B or C and the second flanking sequence in the target nucleic acid can be omitted, i.e., the B or C Domain need not be replaced by a recognition sequence.

In different embodiments, the first flanking region can be located zero, or at least one (e.g., one or two) nucleotide away from and on the 3' side (i.e., downstream) of the uridine in the target nucleic acid. If Domain B is replaced by the second recognition sequence in the modified snoRNA, the second flanking region can be located seven to fourteen nucleotides away from and on the 5' side (i.e., upstream) of the uridine in the target nucleic acid. If Domain C is replaced instead, the second flanking region can be located 0 to 2 nucleotides upstream of the target uridine.

When the recognition sequences of the modified snoRNA are hybridized to the flanking regions of the target nucleic acid, the H or ACA box can be located at least 10, or at least 13, e.g., 14, 15, 16, 17, or 18, nucleotides downstream of a nucleotide in the modified snoRNA that is (i) opposite the uridine (if Domain C is replaced by the second recognition sequence); or (ii) base-paired with a nucleotide located on the 5' end of the modified snoRNA and opposite the uridine (if Domain B is replaced by the second recognition sequence).

In another aspect, the invention features a method of directing pseudouridylation of a selected uridine in a target nucleic acid (e.g., an RNA such as an mRNA, a hybrid RNA/DNA molecule, the RNA genome of a pathogen, or an RNA transcribed from the genome of a pathogen) that includes first and second flanking regions located on either side of the uridine. This method includes the steps of obtaining one of the above-described modified snoRNAs, and contacting the target nucleic acid with the modified snoRNA under conditions sufficient (e.g., in a cell, or in cell or nuclear extracts) for the first and second recognition sequences to hybridize to the first and second flanking regions in the target nucleic acid, respectively, thereby directing pseudouridylation of the uridine.

The method can be carried out in vitro or in a cell. The target nucleic acid can be, for example, in the nucleolus, the nucleoplasm, the cytoplasm, or a mitochondrion of a cell. The cell can be in a mammal or a human patient.

The recognition sequence preferably hybridizes with (e.g., via Watson-Crick base-pairing or other weaker basepairings) at least three nucleotides of the target nucleic acid. Of course, the region of hybridization can contain gaps, provided that a sufficient basepairing interaction is maintained to permit site-specific pseudouridylation. Permissible variations in the level of sequence complementarity can readily be determined by one skilled in the art. The modified snoRNA can contain binding sequences hybridizing to both flanks of the target uridine.

In another aspect, the invention features a modified snoRNA derived from a naturally occurring or artificial H/ACA box snoRNA, where the rRNA-binding sequence of the snoRNA is replaced with a heterologous binding sequence, i.e., a sequence not present in the parent snoRNA, or a sequence present in another region of the parent snoRNA. This modified snoRNA can also be used for directing pseudouridylation of a uridine in a target nucleic acid flanked by regions that are complementary to the heterologous binding sequence in the modified snoRNA.

The invention also provides nucleic acid constructs that contain a coding sequence for a modified snoRNA of the invention.

The invention provides several advantages, as it permits site-specific pseudouridylation of ribonucleotides. Pseudouridylation of specific ribonucleotides in, e.g., RNA molecules, can be used to modulate a wide variety of biological processes. For example, RNA stability, folding, processing, cleavage, and recognition can be modulated by such pseudouridylation or chemical modifications of pseudouridine. Accordingly, the methods of the invention can be used, e.g., to stabilize therapeutic antisense RNAs and ribozymes. In addition, the methods of the invention can be used to modulate gene expression. For example, pseudouridylation of RNA nucleotides can be carried out to, e.g., block pre-mRNA splicing, RNA poly-adenylation, RNA capping, RNA 3'-end formation, or translation of mRNA.

Unless otherwise defined, all technical and scientific terms used herein have the same meaning as commonly understood by one of ordinary skill in the art to which this invention belongs. Although methods and materials similar or equivalent to those described herein can be used in the practice or testing of the invention, suitable methods and materials are described below. All publications and other references mentioned herein are incorporated by reference in their entirety. In case of a conflict, the present specification will control. In addition, the described materials, methods, and examples are illustrative only and are not intended to be limiting.

Other features and advantages of the invention will be apparent from the following detailed description and the claims.

BRIEF DESCRIPTION OF THE DRAWINGS

FIG. 1 is a schematic diagram showing post-transcriptional synthesis of pseudouridine. Pseudouridine is formed from uridine by: (1) cleavage of the $N_1$-$C_1$ glycosyl bond; (2) rotation of the base; and (3) re-attachment through the C5 and $C_1$ carbons.

FIGS. 2A to 2E are schematic representations of consensus structure motifs that correlate snoRNA sequences with sites of pseudouridine ($\psi$) modification. The folded domains A, B and C near either or both ends of the snoRNA represent the portions of the snoRNA that direct pseudouridylation. Alternate domains are enlarged and shown in detail in FIGS. 2D and 2E.

FIG. 6 is a schematic representation of structural elements conserved among 8 different snoRNAs and the corresponding rRNA target regions.

DETAILED DESCRIPTION

Figure 3A:
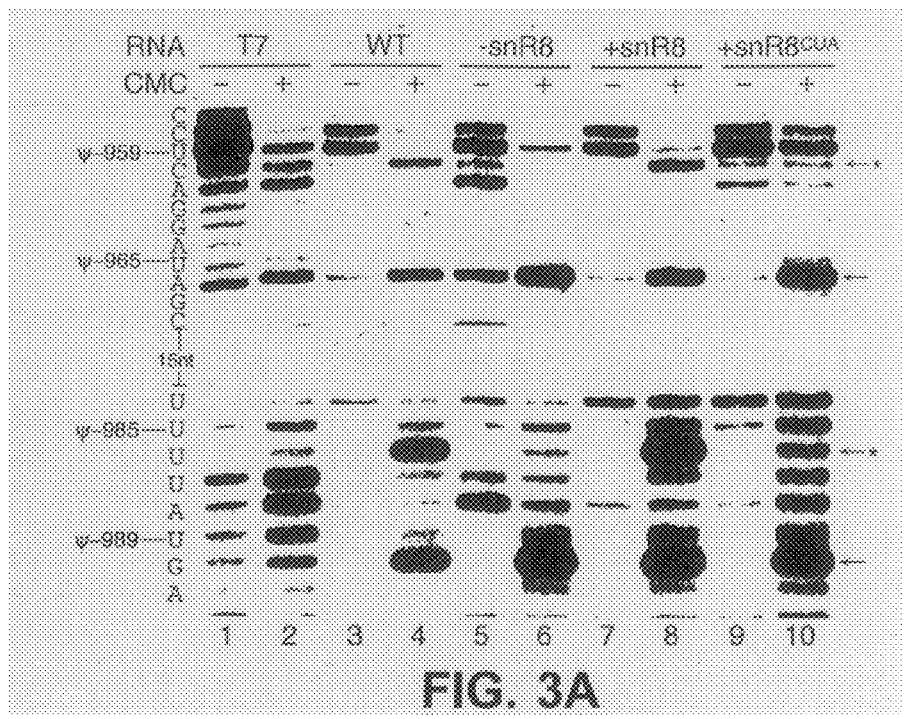
FIGS. 3A to 3C are autoradiographs demonstrating that snoRNAs are required for site-specific synthesis of $\psi$ in eukaryotic rRNA.

The invention provides modified snoRNA molecules that are derived from box H/ACA snoRNAs, and methods of using these modified snoRNAs for site-specific pseudouridylation of specific uridines in nucleic acids. Nucleic acid constructs directing expression of these modified snoRNAs are also included in the invention. Box H/ACA snoRNAs that can be used to generate the new modified snoRNAs include, but are not limited to, those listed in Ganot et al., *Genes & Development*, 11:941–956 (1997), which is incorporated herein by reference in its entirety. Naturally occurring active variants of the ACA element include, but are not limited to, AUA and AAA. Other active variants of the ACA element can be identified using the methods described herein. See, also, Balakin et al., *Cell*, 86:823–834 (1996).

As shown in the experiments described below, pseudouridylation of uridines (FIG. 1) in RNAs in eukaryotic cells depends on the presence of specific box H/ACA snoRNAs. The box H/ACA snoRNAs involved in pseudouridylation typically contain recognition sequences that are complementary to the region in the target RNA flanking the uridine to be pseudouridylated. More specifically, the recognition sequences base-pair with flanking sequences on one or both sides of the target uridine for pseudouridylation to occur.

Typically, the box H/ACA snoRNA molecules form a secondary structure in which the recognition sequences occur in a highly folded region upstream of the box H or box ACA element (FIGS. 2A to 2C). This highly folded region typically includes a terminal loop, two helical stems (designated Domains I and II, respectively), and an internal loop flanked by the helical stems. One of the recognition sequences resides in the upper (upstream) part of the internal loop, and is denominated Domain A. The 3' end of Domain A is generally less than 2 nucleotides away from Domain II. The other recognition sequence either resides in the lower (downstream) part of the internal loop and denominated Domain C (FIG. 2E); or is a portion of the terminal loop and denominated Domain B (FIG. 2D). Like Domain A, Domain C is generally less than 2 nucleotides away from Domain II. Domain B, on the other hand, can be 7 to 14 nucleotides away from Domain II.

The site specificity of pseudouridylation depends also upon the distance between the H or ACA box (or active variants thereof) in the box H/ACA snoRNA and the target uridine in the complex formed by the snoRNA and the target RNA. For pseudouridylation to occur, the distance between the 5' A of the ACA or H box and a snoRNA base pair next to the target uridine should be between 13 and 18 nucleotides, and is typically 14 to 17 nucleotides (see FIGS. 2D and 2E and the Examples, infra). Shifting the location of the ACA box by a certain number of nucleotides results in a change of the pseudouridylation site by the same number of nucleotides, in the same direction. This observation shows that the ACA box is used in selection of the pseudouridylation site.

Box H/ACA snoRNAs can be modified to direct pseudouridylation of novel, specific target uridines by replacing wildtype sequences of Domains A and B or Domains A and C (FIGS. 2D and 2E) that are complementary to rRNA sequences with recognition sequences complementary to regions surrounding the novel, specific target uridines. Further, given the consensus secondary structure of the H/ACA box snoRNAs, one can further modify the snoRNAs by changing nucleotides at certain positions while maintaining the conformation the snoRNAs. For instance, one can change one base pair in the 5' and/or 3' folded domain of a snoRNA to another base pair; or one can eliminate sequences that are not essential for the pseudouridylation function and the production (e.g., stability) of the snoRNA. For example, the terminal loop shown in FIGS. 2A to 2E can be shortened or removed as long as the remaining sequence can form a stable hairpin structure.

Such modified snoRNAs can be made using standard methods, such as polymerase chain reaction methods. See, e.g., Chen et al., *BioTechniques*, 17:657, 1994; Innis et al. (eds.), *PCR Protocols: A Guide to Methods and Applications*, Academic Press, Inc., San Diego, Calif., 1990; Sambrook et al., Molecular Cloning, A Laboratory Manual, 2nd Ed., Cold Spring Harbor Laboratory Press, Cold Spring Harbor, N.Y.; and Ausubel et al., *Current Protocols in Molecular Biology*, Greene Publishing and Wiley-Interscience, New York, N.Y., 1993.

Any snoRNA that normally pseudouridylates an rRNA can be modified to pseudouridylate uridines in other RNAs (e.g., snoRNAs) or non-natural uridine targets in rRNAs in the methods of the invention. For example, human snoRNAs such as U17/E1, E2, E3, U19, and U23, or yeast snoRNAs such as snR3, snR5, snR8, snR9, and snR10, can be used (see, e.g., Balakin et al., supra).

Any uridine that can be positioned in the appropriate context of a basepairing interaction with a modified snoRNA can be pseudouridylated using the methods of the invention. Such a uridine can be present in RNA especially nucleolar RNAs such as rRNA and snoRNA. The target uridine can also be present in transfer RNA, decoy RNAS, small RNA components of the pre-mRNA splicing apparatus (snRNAs), signal recognition particle (SRP), the RNaseP complex. In addition, the uridine targets can be in the context of non-natural molecules made biologically or chemically, and also with materials that contain chemical constituents that mimic the essential relevant components of RNAs. For instance, the target uridine can be located within a DNA-RNA hybrid molecule.

The methods of the invention can be used to modify RNAs transcribed from altered genes, such as genes containing mutations, e.g., point mutations or chromosomal transversions. The methods can also be used to pseudouridylate RNA that is present in a cell as a result of an infection, such as a bacterial or viral infection. For example, it may be desirable to impede the expression and/or replication of such pathogen-derived RNAs. As a specific example, the methods of the invention can be used to affect steps of viral RNA maturation that involve RNA cleavage. In combination with certain biochemical detection procedures, the present methods can also be used to detect the presence of altered genes for diagnostic purposes.

The methods of the invention can also be used to pseudouridylate RNA that is present in a cell as a result of gene therapy. For example, RNAs produced by transcription of genes that (1) were introduced into cells by gene therapy and (2) encode therapeutic proteins, ribozymes, or antisense RNAs can be stabilized by such pseudouridylation.

Pseudouridine has three distinctive features compared to unmodified uridine: (1) The C-C glycosyl bond is more flexible than the conventional C—N bond, and can therefore influence RNA folding or conformational changes; (2) the N-1 proton can serve as an extra H-bond donor in tertiary folding of the RNA or in specific protein:RNA interactions; and (3) the N-1 position has high acyl group transfer potential. Thus, pseudouridylation can be used to alter folding of the RNA, as well as interaction of the RNA with other molecules, including other RNAs, DNA, proteins, other classes of cellular molecules and components, and non-biological materials.

Applications of the invention include, but are not limited to altering the physical, biological, and chemical properties of RNAs in cells or in vitro. Potential biological applications include: (1) altering natural reactions associated with the production of mature RNA molecules, including site-specific processing (cleavage), formation of modified nucleotides, editing (changing) the sequence of transcribed canonical nucleotides in RNA polymers and addition of "cap" structures and poly-A "tails"; (2) altering the expression of natural and artificial genes; (3) impairing infection processes involving viruses or other agents, by altering replication, maturation, packaging and utilization of the foreign RNA, including genetic expression of RNAs involved in infection. In this context, it has been shown that pseudouridylation of certain transfer RNAs can alter translation activity in vivo (Hagervall et al., *Biochem. Biophys. Acta*, 1050:263–266, 1990; Tsui et al., *J. Bacteriol.*, 173:7395–7400, 1991). Thus, the new modified snoRNAs can be used to target transfer RNAs to affect translation.

Another application of the invention is to confer useful biochemical or biophysical properties (e.g., increased or decreased stability, altered conformation, or improved detectability) to RNA by modifying pseudouridine(s) that have been introduced into the RNA molecule. For instance, to detect the presence of U mutation in an mRNA for diagnostic purposes, the uridine is first converted into pseudouridine, which is then covalently labeled with a detectable biochemical tag.

snoRNA-directed pseudouridylation can be carried out in cell-free conditions. Such methods can include modification of natural or artificial RNAs in extracts from cells or reactions that contain few or no natural biological molecules. Pseudouridylation in the latter case would be effected by biological mimicry, using reaction components that feature or are based on elements of the natural biological machinery.

Nuclear extracts, such as fractionated nuclear extracts, which are prepared using standard methods, can be used to carry out in vitro pseudouridylation by modified snoRNAs. The utility of such extracts may depend on the presence of snoRNP protein components that may be required for pseudouridylation. In addition, a pseudouridine synthase may be required. These enzymes create pseudouridines in a site-specific fashion in *E. coli* rRNA and *E. coli* and yeast tRNA (Wrzesinski et al., *RNA*, 1:437–448, 1995).

Use

The modified snoRNAs of the invention can be introduced into cells using standard gene therapy methods. For example, the snoRNAs of the invention can be produced within a target cell by transcription of a nucleic acid molecule containing a promoter sequence operably linked to a sequence encoding the modified snoRNA. In this method, the nucleic acid molecule is contained within a non-replicating linear or circular DNA or RNA molecule, is contained within an autonomously replicating plasmid or viral vector, or is integrated into the host genome. Any vector that can transfect a target cell can be used in the invention. Preferred vectors are viral vectors, including those derived from retroviruses (see, e.g., WO89/07136; Rosenberg et al., *N. Eng. J. Med.*, 323(9):570–578, 1990), adenovirus (see, e.g., Morsey et al., *J. Cell. Biochem., Supp.* 17E, 1993; Graham et al., in Murray, ed., *Methods in Molecular Biology: Gene Transfer and Expression Protocols*, 7:109–128, 1991), adeno-associated virus (Kotin et al., *Proc. Natl. Acad. Sci. USA*, 87:2211–2215, 1990), replication defective herpes simplex viruses (HSV; Lu et al., Abstract, page 66, Abstracts of the Meeting on Gene Therapy, Sep. 22–26, 1992, Cold Spring Harbor Laboratory, Cold Spring Harbor, N.Y.), replication-defective hepatitis viruses (e.g., HBV and HCV), and any modified versions of these vectors. Methods for constructing expression vectors are well known in the art (see, e.g., Sambrook et al. and Ausubel et al, supra).

Appropriate regulatory sequences (e.g., promoters and enhancers) can be inserted into such vectors using methods known to those skilled in the art, for example, by homologous recombination (Graham et al., *J. Gen. Virol.* 36:59–72, 1977), or other appropriate methods (see, e.g., Sambrook et al., supra). Promoters are inserted into the vectors so that they are operably linked 5' to the nucleic acid sequence encoding the antisense oligonucleotide. Any promoter that is capable of directing initiation of transcription in a eukaryotic cell can be used in the invention. For example, non-tissue specific promoters, such as the cytomegalovirus (DeBernardi et al., *Proc. Natl. Acad. Sci. USA*, 88:9257–9261, 1991, and references therein), mouse metallothionine I gene (Hammer, et al., *J. Mol. Appl. Gen.*, 1:273–288, 1982), HSV thymidine kinase (McKnight, *Cell*, 31:355–365 1982), and SV40 early (Benoist et al., *Nature*, 290:304–310, 1981) promoters can be used. Tissue-specific promoters can also be selected, depending on the type of cell in which expression of the modified snoRNA is desired.

Viral promoters and enhancers, such as those from cytomegalovirus, herpes simplex viruses (types I and II), hepatitis viruses (A, B, and C), and Rous sarcoma virus (RSV; Fang et al., *Hepatoloqy*, 10:781–787, 1989), can also be used in the invention.

Recombinant vectors containing nucleic acid sequences encoding modified snoRNAs can be used in therapeutic compositions for, e.g., treating conditions associated with undesired expression of an mRNA or replication of RNA genomes (e.g., viral infections), or for stabilizing ribozymes or antisense molecules introduced by gene therapy. The therapeutic compositions of the invention can be used alone or in admixture, or in chemical combination, with one or more materials, including other recombinant vectors, materials that increase the biological stability of the recombinant vectors, or materials that increase the ability of the therapeutic compositions to specifically penetrate the relevant cell type. The therapeutic compositions of the invention are administered in pharmaceutically acceptable carriers (e.g., physiological saline), which are selected on the basis of the mode and route of administration, and standard pharmaceutical practice. Suitable pharmaceutical carriers, as well as pharmaceutical necessities for use in pharmaceutical formulations, are described in *Remington's Pharmaceutical Sciences*, a standard reference text in this field, and in the USP/NF.

The therapeutic compositions of the invention are administered in dosages determined to be appropriate by one skilled in the art. An appropriate dosage is one that effects a desired result, e.g., a reduction in a symptom of a disease sought to be treated. It is expected that the dosages will vary, depending upon the pharmacokinetic and pharmacodynamic characteristics of the particular agent, and its mode and route of administration, as well as the age, weight, and health of the recipient; the nature and extent of any relevant disease; the frequency and duration of the treatment; the type of, if any, concurrent therapy; and the desired effect. It is expected that a useful dosage contains between about 0.1 to 100 mg of active ingredient per kilogram of body weight. Ordinarily, 0.5 to 50 mg, and preferably, 1 to 10 mg of active ingredient per kilogram of body weight per day given in divided doses, or in sustained release form, is appropriate.

The therapeutic compositions of the invention can be administered to a patient by any appropriate mode, e.g., parenterally, intraperitoneally, orally, topically (e.g., with dimethyl sulfoxide (DMSO)), or intravenously, as determined by one skilled in the art. Alternatively, it may by necessary to administer the treatment surgically to the target tissue. The treatments of the invention can be repeated as needed, as determined by one skilled in the art.

The invention also includes any other methods that accomplish in vivo transfer of nucleic acids into eukaryotic cells. For example, nucleic acids encoding snoRNAs (or snoRNAs themselves or snoRNA-protein complexes (snoRNPs)) can be packaged into liposomes, non-viral nucleic acid-based vectors, erythrocyte ghosts, or microspheres (e.g., microparticles; see, e.g., U.S. Pat. No. 4,789,734; U.S. Pat. No. 4,925,673; U.S. Pat. No. 3,625,214; Gregoriadis, *Drug Carriers in Biology and Medicine*, pp. 287–341 (Academic Press, 1979)). Further, delivery of snoRNAs can be accomplished by direct injection of the snoRNAs into target tissues, for example, in a calcium phosphate precipitate or coupled with lipids.

Exogenously provided snoRNAs can contain modified nucleotides, e.g., modified nucleotides that enhance stability. For example, the snoRNAs can contain inter-nucleotide linkages other than phosphodiester bonds, such as phosphorothioate, methylphosphonate, methylphosphodiester, phosphorodithioate, phosphoramidate, phosphotriester, or phosphate ester linkages (Uhlman et al., *Chem. Rev.*, 90(4):544–584, 1990; Tidd et al., *Anticancer Research*, 10:1169, 1990). snoRNA stability can also be increased by incorporating 3'-deoxythymidine or 2'-substituted nucleotides (substituted with, e.g., alkyl groups) into the snoRNAs during synthesis, by providing the snoRNAs as phenylisourea derivatives, or by having other molecules, such as aminoacridine or polylysine, linked to the 3' ends of the snoRNAs (see, e.g., Tidd et al, supra). Modifications of the RNA nucleotides of the snoRNAs of the invention may be present throughout the snoRNA, or in selected regions, e.g., the 5' and/or 3' ends. The snoRNAs can also be modified to increase their ability to penetrate the target tissue by, e.g., coupling them to lipophilic compounds. The snoRNAs of the invention can be made by standard methods known in the art, including standard chemical synthesis and transcription of DNA encoding them. In addition, snoRNAs can be targeted to particular cells by coupling them to ligands specific for receptors on the cell surface of a target cell. snoRNAs can also be targeted to specific cell types by being conjugated to monoclonal antibodies that specifically bind to cell-type-specific receptors.

The method of the invention can be applied to any eukaryotic organism ranging from yeast to humans. For example, the invention can be applied in methods to pseudouridylate RNAs in fungi for treating a fungal infection (e.g., *Candida albicans, Blastomyces dermatitidus*, and *Histoplasma capsulatum*), in a patient. In these methods, snoRNAs can be targeted to fungal RNA sequences which, when pseudouridylated, reduce, e.g., the rate of cell division. For treatment of some of the manifestations of these infections, topical administration may be desired. For topical administration, e.g., a therapeutically effective amount of one or more of the expression constructs of the invention is applied to the desired site on the skin, preferably in combination with a pharmaceutically acceptable carrier, e.g., a spreadable cream, gel, lotion, or ointment, or a liquid such as saline. For use on the skin, the penetration of the snoRNA expression constructs into the tissue may be accomplished by a variety of methods known to those of ordinary skill in this field. Furthermore, the snoRNA expression constructs may be incorporated into a transdermal patch that is applied to the skin. Preferably, the penetration resulting from these methods is enhanced with a chemical transdermal delivery agent such as dimethyl sulfoxide) or the nonionic surfactant, n-decylmethyl sulfoxide), as described in Choi et al., *Pharmaceutical Res.*, 7(11):1099, 1990. Dosages for a therapeutically effective amount for topical application would be in the range of 100 ng to 10 mg per treated surface area per day.

EXAMPLES

The following experimental data and protocols are used as an example to illustrate, but not limit, the modified snoRNAs, expression constructs, and methods of the invention.

Example 1

Ten snoRNAs are Required for Site-Specific Formation of Pseudouridine ($\psi$) at Eleven Positions in rRNA At the onset of our study 20 yeast ACA snoRNAs had been identified. Of these, 17 had been characterized genetically and 16 were known to be non-essential for growth. The essential species is snR30, which is required for rRNA processing (Morrissey et al., *Mol. Cell. Biol.* 13:2469–2477, 1993). We have examined patterns of pseudouridine modification for each of the 16 dispensable snoRNAs, using total RNA from cells containing disrupted snoRNA genes. Modification was evaluated by a primer extension assay after treating the RNA with N-cyclohexyl-N'-$\beta$-(4-methylmorpholinium)-ethylcarbodiimide p-tosylate (CMC). In this procedure the presence of pseudouridine is reflected as a pause in the ladder of extension products (Bakin et al., *Biochemistry*, 32:9754–9762, 1993).

Fully modified yeast rRNA contains 43 residues, 13 in the small subunit (SSU) RNA and 30 in the large subunit (LSU) RNA. Each site of modification has been determined precisely (the last 20–40 nt of each rRNA have not been analyzed). Thus far, we have examined 30 of the 43 sites (70%) for all 16 ACA snoRNAs evaluated (see Experimental Procedures). Deficiencies in pseudouridine have been observed for 10 of the 16 snoRNAs tested (63%). The modification data obtained for 3 snoRNAs are shown in FIGS. 3A–3C and the findings for all 10 species are summarized in Table 1.

Figure 3B:
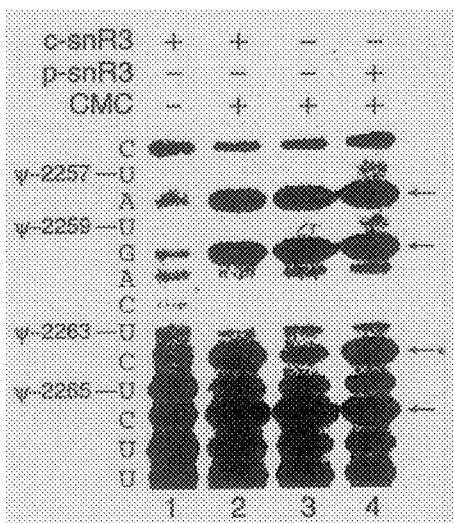
Figure 3C:
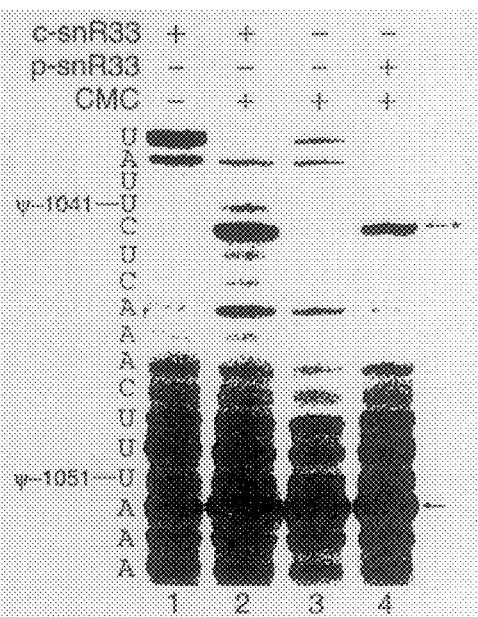

In FIGS. 3A to 3C, formation of $\psi$ was examined by a reverse transcription primer extension assay following treatment of isolated total RNA with CMC (Bakin et al., *Biochemistry*, 32:9754–9762, 1993; see Experimental Procedures). The primer extension products were fractionated on polyacrylamide gel and visualized by autoradiogram. The presence of a $\psi$ is indicated by the occurrence of a strong band in the gel at a position one nucleotide prior to the modified nucleotide. This band is normally absent or much less pronounced for CMC-untreated samples. Results are shown for three yeast strains, each depleted of a different snoRNA. Only the affected rRNA regions are shown. FIG. 3A shows results obtained with several modified snoRNAs derived from snR8, and the primer used for reverse transcription was complementary to 1010–1029 of LSU rRNA. FIG. 3B shows results obtained with several modified snoRNAs derived from snR3, and the reverse was primer complementary to 2274–2293 of LSU rRNA. FIG. 3C shows results obtained with modified snoRNAs derived from snR33, and the reverse primer was complementary to 1065–1084 of LSU rRNA.

In FIG. 3A, the RNA templates used for reverse transcription were: in vitro synthesized unmodified 25S rRNA fragment (939 to 1159) with an extra G from the T7 promoter at the 5' end (T7 lanes); RNA from wild type strain YS602 with no snoRNA depletions (WT lanes); RNA from a strain (YD8, see Experimental Procedures, infra) containing a genomic snR8 disruption and no plasmid (–snR8 lanes); RNA from the snR8 disruption strain transformed with a plasmid-encoded wild type snR8 allele (+snR8); and RNA from the snR8 disruption strain transformed with a plasmid-encoded snR8 allele in which the conserved ACA box (variant AUA in this case) was changed to CUA [+snR8$^{CUA}$; this mutation was shown to disrupt the accumulation of ACA RNAs (see, e.g., Balakin et al., *Cell*, 86:823–834, 1996)].

In FIGS. 3B and 3C, the presence (+) or absence (–) of chromosomal or plasmid-encoded snR3 and snR33 genes is indicated by c-snR3, c-snR33 or p-snR3, p-snR33, respectively. To simplify the figures, FIGS. 3B and 3C do not show the negative results obtained for the in vitro transcribed rRNA fragment, nor are the lanes from samples not treated with CMC shown, except for the undisrupted wild type strain.

For all of FIGS. 3A–3C, the nucleotide positions are determined by counting from the 3' end of each primer. Pseudouridine positions are identified next to the sequences at the left, and the corresponding reverse transcript bands are indicated with arrows at the right. Arrows marked with asterisks denote positions at which $\psi$ is lost following disruption of a specific snoRNA gene. CMC treatment is indicated by –(no CMC) and +(treated with CMC). Sites of $\psi$ formation shown to depend on snoRNA are summarized in

TABLE 1

SnoRNAs required for ψ synthesis in yeast rRNA

|  | snR3 | snR8 | snR10 | snR31 | snR32 | snR33 | snR34 | snR37 | snR42 | snR46 |
|---|---|---|---|---|---|---|---|---|---|---|
| rRNA | LSU | LSU | LSU | SSU | LSU | LSU | LSU | LSU | LSU | LSU |
| ψposition | 2263 | 985 (959) | 2919 | 1000 | 2190 | 1041 | 2876 | (2940) | 2971 | (2861) |

Numbering of ψ nucleosides is according to Bakin and Ofengand (Bakin et al., Nucleic Acids Res., 23: 3290–3294, 1995; Bakin et al., Biochemistry, 33: 13475–13483, 1994). Eight of eleven ψ sites conform to the consensus motif shown in FIG. 2D; positions which do not conform are in parentheses.

As shown in FIGS. 3A–3C, modification was rescued for the first three snoRNAs showing effects (snR3, snR8, snR33) by introducing a wild-type snoRNA gene on a single-copy CEN plasmid. The snR8 dependence was also demonstrated with a snoRNA gene containing mutations in the ACA box known to block snoRNA synthesis. As expected, the mutant snR8 gene failed to rescue pseudouridine (ψ) synthesis in the test strain (FIG. 3A, lane 10). The snR8 species, which effects two sites of modification, contains a non-canonical ACA box (AUA). AUA and AAA are natural variants, both active in snoRNA synthesis. To determine if the broader site specificity is related to the atypical box element, we converted the AUA triplet to ACA. This mutation did not alter the modification pattern (results not shown).

All of the deficiencies observed were: (1) site-specific and (2) specific to individual snoRNAs (Table 1). Nine of the snoRNAs are required for the formation of single residues at different locations, and the tenth species, snR8, is required for synthesis of two ψs separated by 25 nucleotides. No deficiencies were detected for two box C/D snoRNAs included as controls. Taken together, the results demonstrate that ACA snoRNAs are indeed required for site-specific modification and further suggest that this requirement may be related to site selection.

Example 2

Common Structure Motifs Between the snoRNA and rRNA Target Sequence Predict the snoRNA Requirement Involves Site Selection Our search for a RNA structure motif that correlates snoRNAs with modification focused on identifying potential complementarities between the snoRNAs and sites of modification. We considered the folding properties of the snoRNAs first, and then searched for short complementarities between conserved snoRNA domains and the rRNA target regions. Two common motifs became apparent after several snoRNAs were linked to specific sites of modification.

In the course of defining the family of H/ACA snoRNAs, we developed secondary folding models for each known species. This analysis was based on use of experimentally derived secondary structures to evaluate models developed by computer folding analysis. The experimental structures were generated by direct probing of two H/ACA snoRNAs (yeast snR11, human and mouse U19). Results from this analysis revealed that most of the RNAs can be folded into a common core structure (FIGS. 2A–2C). This structure includes: (1) a highly folded region near the 5' end; (2) a single-stranded hinge region with a putative H box (i.e, ANANNA, where N can be any nucleotide but the first N often is G) at the proximal end; and (3) a highly folded region at the 3' end which is followed by the ACA box. The folded regions immediately upstream of boxes H and ACA are strikingly similar.

FIGS. 2A to 2C show this common secondary core structure. The figures indicate the locations of boxes H and ACA found in most box H/ACA snoRNAs. Segments labeled "A," "B," and "C" represent Domains A, B, and C, respectively, and are complementary to rRNA sequences flanking the site of modification (see also FIGS. 2D and 2E). Conserved snoRNA helices are identified as Domains I and II.

FIGS. 2D and 2E show that sequence elements in the 5' and/or 3' portion of the snoRNA can potentially base pair with rRNA sequences adjacent to a site of ψ modification. The ACA and H boxes are represented as an ANA box, where N is any nucleotide. The common snoRNA-rRNA motif includes: (1) regions of snoRNA:rRNA complementarity that flank the site of ψ modification (i.e., Domains A and B, and/or Domains A and C); (2) snoRNA helical segments (Domains I and II), one of which occurs between the elements complementary to rRNA (Domain II); and (3) the ANA box. In the motif shown in FIG. 2D, the ANA box occurs approximately 15 nucleotides from the site of ψ formation. In the motif shown in FIG. 2E, the ANA box occurs about 14 nucleotides from the site of ψ formation. The consensus motifs were developed from comparisons of hypothetical snoRNA folding patterns and searches for positionally conserved complementarities between snoRNAs and rRNA sites of ψ modification.

A search of the folded snoRNAs then revealed complementarities with the rRNA modification regions that are positionally conserved in both RNAs. Consensus motifs emerged that accommodate all of the H/ACA snoRNAs involved in ψ formation (FIGS. 2A–2C). The conserved features which define the motif include: (1) two complementarities between the snoRNA and rRNA region of modification (Domains A and B and/or Domains A and C); (2) a single-stranded rRNA region which contains the site of modification; and (3) two snoRNA helices (Domains I and II). While all snoRNAs required for ψ synthesis can be accommodated by the consensus motifs, the best fit is obtained by the motif depicted in FIG. 2E. These results suggest that these common motifs play a direct role in site selection.

FIG. 6 illustrates the alignments between several snoRNAs and their target rRNAs. These alignments are consistent with the motif shown in FIG. 2D. The ACA box is used as a common reference point. The snoRNA regions depicted occur in the 3' portions of the molecules. In some cases, gaps have been inserted between complementary elements in the snoRNA to achieve simple alignments. Missing snoRNA segments are denoted as broken lines and gaps as solid lines. Conventional base-pairing (including G-U) is denoted with vertical lines, and G-A pairs with small circles. The position of the ψ affected by snoRNA depletion is shown for each snoRNA-rRNA pair. Note that the ψ is always located either immediately adjacent to the Domain A complementarity (FIG. 2D) or 1 nucleotide away. Also the distance between the ψ and ACA box is an almost constant 15 nucleotides, counting to the base pair in snoRNA Domain II which is opposite the ψ in this configuration; snoR8 is an exception, with a spacing estimated at approximately 17 nucleotides, however, the nucleotides underlined in snR8 could form a short stem structure and yield a shorter spacing (FIG. 4).

The motifs predict that the snoRNAs bind to the modification region through the complementary elements which flank the site of modification. We note that the distance between Domain A and the target uridine is no greater than one nucleotide in every case. Good complementarity exists for every snoRNA:rRNA pair, although with different base pairing potentials. The Domain A complementarity varies from 6–11 base pairs including non-Watson-Crick A-G pairs. The complementarity at Domain B ranges from 6–12 base pairs for 6 of the 8 snoRNAs. The complementarity at Domain C ranges from 6–11 basepairs. No substantial Domain B complementarity occurs for snR32 and snR34, but interestingly, the base pairing potential through Domain A is markedly enhanced in these cases. Binding of snoRNA to the target region could influence site selection through docking of the pseudouridine synthase. The snoRNA can also be imagined to influence modification in other ways, for example, by inducing conformational changes required for the reaction.

The position of the H and ACA boxes relative to the site of modification is also striking. This spacing is a virtually constant distance of 15 nucleotides (see the two-dimensional format depicted in FIGS. 2D and 2E). This observation suggests that the H and ACA boxes be determinants in site selection (FIG. 4B). The distance is exactly 15 nucleotides for 7 of the 8 individual snoRNAs examined. The spacing for the eighth snoRNA snR8 appears to be 17 nucleotides.

In all the H/ACA snoRNAs examined, the elements proposed to be involved in the interaction with rRNA occur in the 5' and/or 3' portion of the snoRNA. These portions contain a main stem defined by the conserved snoRNA helices (Domains I and II). The two sequences complementary to rRNA are predicted to be single stranded or mostly so. In addition to the implied involvement in ψ formation, portions of the 3' stem-loop domain of the snoRNA and the adjoining ACA box are known to be required for synthesis of the snoRNA itself (Balakin et al., Cell, 86:823–834, 1996). Thus, some or all of these elements could be involved in more than one process.

Example 3

Mutational Results Indicate that the Motif is Relevant

Two major predictions of the motifs have been subjected to preliminary experimental tests: (1) that base pairing between the snoRNA and rRNA is essential for ψ formation; and (2) that the distance between the ACA box and site of modification is a key determinant in site selection. The putative snoRNA:rRNA interaction was assessed by weakening the implied Domain A interaction, and the importance of the ACA-ψ spacing was examined by altering this distance. These analyses were conducted by mutating snR8, which is required for two modifications in the LSU rRNA. One modification site (ψ985) was found to conform to the motifs shown in FIGS. 2D and 2E. This snoRNA was selected because the ψ985 modification occurs within a sequence of four uridines, which offers the potential to detect changes in site specificity through modification of a neighboring uridine.

Figure 4A:
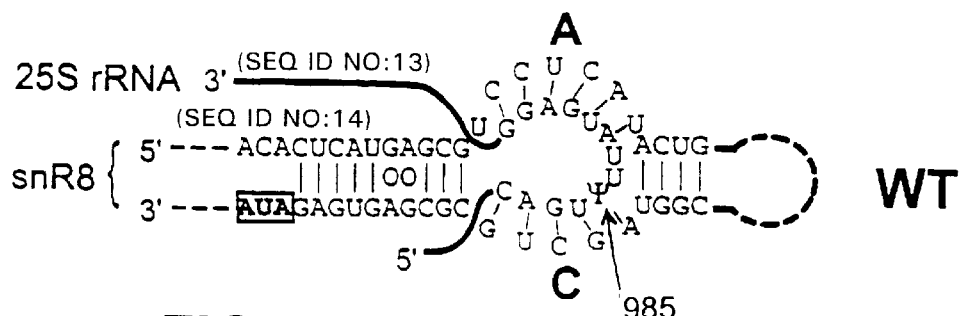
FIGS. 4A to 4C are schematic representations of partial ribonucleotide sequences of the snoRNAs used in mutational analysis of the snoRNA structural motifs.
Figure 4B:
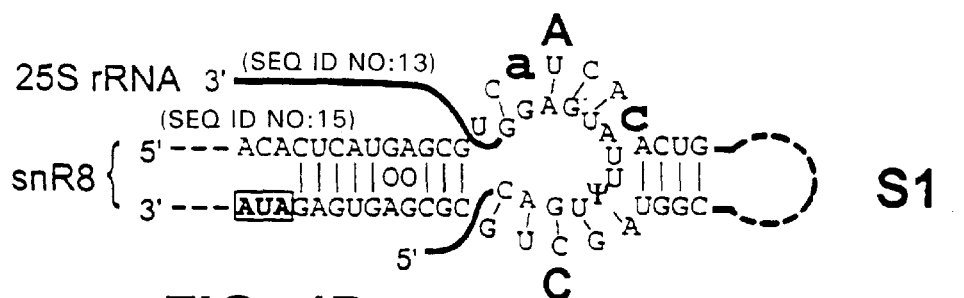
Figure 4C:
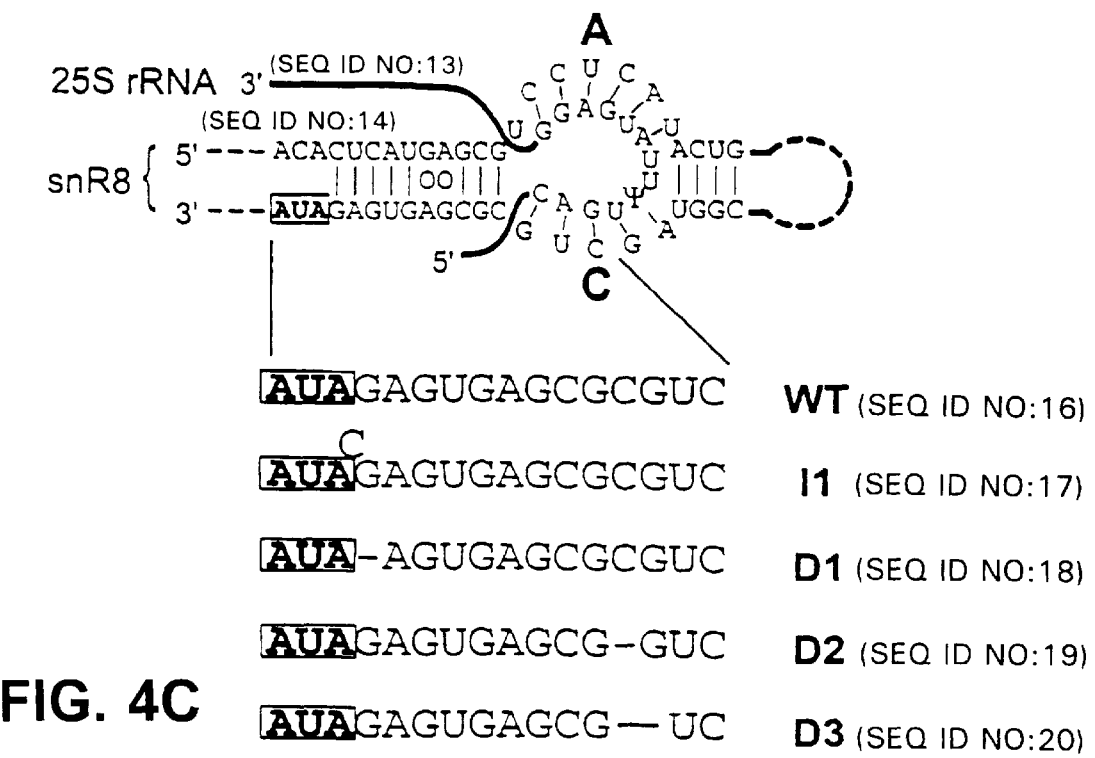

FIGS. 4A–4C demonstrate the importance of the complementarity between snoRNA and rRNA. The relative position of the ACA box was examined by altering yeast snR8. Only the central part of the motif is shown in these figures. The predicted snoRNA:rRNA interaction was impaired by substituting 2 nucleotides in the Domain A element of snR8 (S1; FIG. 4B). The influence of the ACA box position was assessed by introducing a single nucleotide insertion (I1) or deletions of one or two nucleotides on either side of Domain I (D1–D3; FIG. 4C). FIG. 4A shows the secondary structure of a 3' portion of the wild type snR8; FIG. 4B shows the sequence of domain A with the two-base S1 substitution; and FIG. 4C lists several insertion and deletion mutations (I1, D1, D2, and D3) introduced to the 3' portion of wild type snR8. The altered bases in the S1 substitution are shown in boldface lower case letters. The I1 insertion is indicated above the wild type sequence and the deletions are shown as gaps (solid lines). The mutations described in FIGS. 4B and 4C were created in a plasmid-encoded SNR8 gene and the effects examined in a test strain (YD8) containing an inactive chromosomal SNR8 gene.

Figure 5:
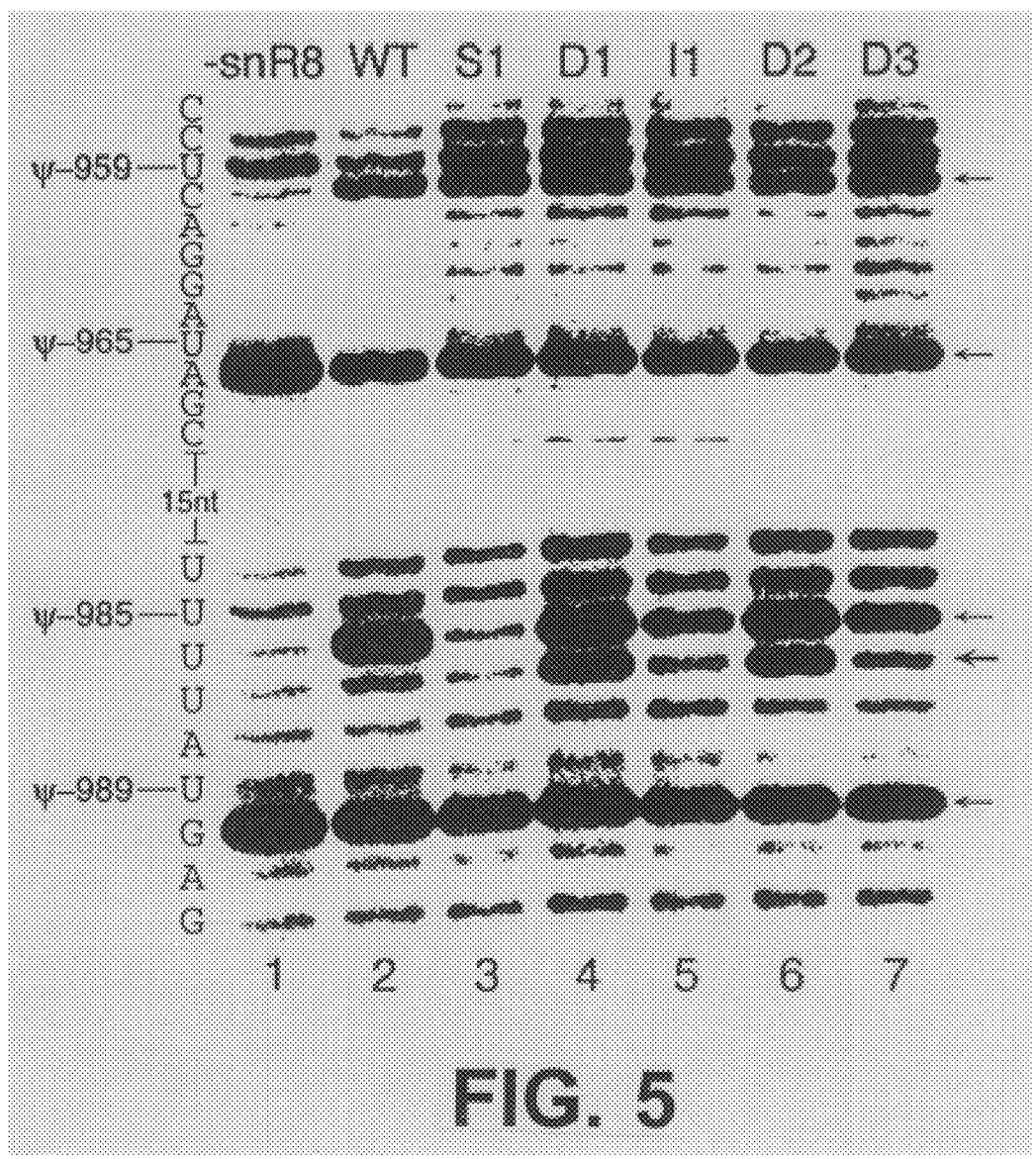
FIG. 5 is an autoradiograph showing that snoRNA mutations affect both activity and specificity of $\psi$ synthesis.

The autoradiogram in FIG. 5 shows the results of the mutations on pseudouridylation of the target sequence. Synthesis of ψ was examined by the CMC-primer extension assay procedure. The snoRNA mutations are identified above each lane using the abbreviations defined in FIGS. 4A–4C. Data are shown for the rRNA regions which normally contain ψ modifications at positions 959, 966, 985 and 989. The sites of modification are indicated at the left and the corresponding reverse transcript bands are indicated by arrows at the right. A novel site of ψ modification occurred with mutations D1 and D2, at position U986 (bold arrow). Control samples included RNA from the test strain (YD8, lane 1) and the same strain transformed with a plasmid containing a wild-type SNR8 gene (WT, lane 2).

The Domain A complementarity of 7 base pairs was weakened with a two-nucleotide substitution mutation (FIG. 4B). This alteration blocked synthesis of ψ985, but had no effect on formation of ψ959 (FIG. 5, lane 3). Loss of activity at the U985 site supports the view that modification indeed depends on interaction of the snoRNA with the rRNA target region. The fact that only this site was affected indicates that the ψ959 modification does not depend on formation of ψ985. This result also suggests that the requirement for snR8 at the non-motif site may be indirect or involve different snoRNA determinants.

The spatial relationship between the ACA box and target nucleoside was altered with insertions and deletions of one or two nucleotides (FIG. 4C). These mutations were made in two regions: (1) between the ACA box and Domain I helix, and (2) at the opposite end of Domain I. We expected these mutations to either shift the site of modification or reduce the yield of ψ. Consistent with this prediction, the pattern of modification was altered in every case, although not in a simple way (FIG. 5, Table 2). Some mutations led to alteration in site specificity and others to reduced activity at the normal U985 site. Modification at the second natural site (U959) occurred normally in each case.

A one nucleotide deletion immediately upstream of the ACA box (D1, FIG. 4C) did not have a noticeable effect on formation of ψ985, but did result in synthesis of ψ at a novel site, at an adjacent uridine (U986 FIG. 5, lane 4; Table 2). The yield at the novel site was estimated to be about 60% of that detected at the U985 position. A similar shift in specificity and yield was also obtained for a one nucleotide deletion located at the other end of the Domain I helix (D2, FIG. 4C; FIG. 5, lane 6). If the U985 site is fully modified in wild-type cells, the yield data suggest that some of the rRNA molecules characterized are modified at both positions 985 and 986.

TABLE 2

Effect of moving the ACA box on ψ formation

| snR8 variant | d(nt) | Δd (nt) | $U_{987}$ | $U_{986}$ | $U_{985}$ | $U_{984}$ |
|---|---|---|---|---|---|---|
| WT | 17 | 0 | | | ++ | |
| I1 | 18 | +1 | | | +/− | |
| D1 | 16 | −1 | | + | ++ | |
| D2 | 16 | −1 | | + | ++ | |
| D3 | 15 | −2 | | | + | |

Insertion (I) and deletion (D) mutations are identified in FIGS. 4A–4C.
d, distance between the ACA box and snR8 base pair (Domain II) opposite the site of rRNA modification at ψ985.
Δd, change in d.
Extent of ψ formation is indicated by: ++, 100%; +, ~60%, and; +/−, ~30%, where 100% refers to the wild-type level at position 985.

Two other mutations reduced the yield of ψ985 without creating a new site of modification. An insertion of one nucleotide (I1) immediately upstream of the ACA box reduced the yield of ψ985 to about 30% of the normal level. A two nucleotide deletion (D3) at the opposite end at the Domain I helix reduced the modification level to about 60% of the normal level (FIG. 4C; FIG. 5, lanes 5 and 7). If distance from the ACA box were the sole determinant in site selection, any new modification resulting from insertions and deletions would be expected to occur in a consistent pattern. A new site was seen for two deletions of one nucleotide, but not for a one nucleotide insertion or two nucleotide deletion. These results are consistent with the RNA pairing schemes shown in FIGS. 2D and 2E. Together, the data support the view that site selection is influenced by the spatial relationship of the target uridine and the H or ACA box.

None of the snR8 mutations analyzed are predicted to perturb the secondary folding of the snoRNA in a substantial way, and northern assays indicated that snR8 was present at normal levels for all mutants used in this analysis. The mutations could, of course, affect tertiary folding and the structure and activity of the final snoRNP complex. The fact that ψ959 was formed in each case suggests that the snoRNP is at least partly functional regardless of its role at ψ985. On this basis, we believe that it is reasonable to suggest that the defects in ψ985 formation reflect alterations in snoRNA determinants required for modification.

Example 4

Experimental Procedures

The following describes the experimental procedures for conducting the experiments of Examples 1 to 3.

Yeast strains

Wild type, YS602, MATα, ade2, his3, trp1, ura3, leu2; YD3, snr3::LEU2, ade2, his⁻, trp1, ura3, leu2; YD8, snr8::HIS3, ade2, his3, trp1, ura3, leu2; YD10, snr10::LEU2, ade2, his3, trp1, ura3, leu2; YD31, snr31::URA3, ade2, his3, trp1, ura3, leu2; YD32, snr32::his3, ade2, his3, trp1, ura3, leu2; YD33, snr33::ura3, ade2, his3, trp1, ura3, leu2; YD34, snr34::LEU2, ade2, his3, trp1, ura3, leu2; YD37, snr37::URA3, ade2, his3, trp1, ura3, leu2; YD42, snr42::his3, ade2, his3, trp1, ura3, leu2; YD46, snr46::his3, ade2, his3, trp1, ura3, leu2; RL5, MATα, trp1, his3, his4, ura3, leu2, lys2, ade2, snr3::LEU2, snr4::URA3, snr5::TRP1, snr8::HIS3, snr9::URA3, and; RL60, MATα, trp1, his3, his4, ura3, leu2, lys2, ade2, snr3::LEU2, snr4::URA3, snr5::TRP1, snr8::HIS3, snr9::URA3, snr10::LEU2. RL5 and RL60 are from Parker et al., Mol. Cell. Biol. 8:3150–3159, 1988. Strains YD31, YD32, YD33, YD34, YD36, from this laboratory, have been previously described (Balakin et al., Nucleic Acids Res. 21:5391–5397, 1993; Samarsky et al., Nucleic Acids Res. 23:2548–2554, 1995). Strains YD37, YD42, YD46 were constructed by Andrey G. Balakin. YD3 and YD8 were derived by mating wild type YS602 with strain RL5 which contains five snoRNA gene disruptions.

After sporulation, isolates containing single snoRNA gene disruptions were selected using the corresponding markers and identified positively by Northern analysis. Strain YD10, containing a disrupted snR10 gene locus, was created by PCR amplification of DNA from strain RL60 and transforming YS602 cells with this PCR fragment. Primers used for the PCR were 5'-CCATGTCTTGAAGCTTCTTC-3' (SEQ ID NO:1) and 5'-CGCGGATCCTGCAGCATTCCAAGCCACTC-3' (SEQ ID NO:2), which correspond to flanking regions of the SNR10 gene. Loss of snR10 in YD10 was verified by northern analysis. Six additional test strains devoid of specific H/ACA snoRNAs have also been analyzed, with positive results. Genotypes of the strains are not shown. The snoRNA species and sites of modification affected (in parenthesis) are: snR5(nucleotides 1003 and 1123 in 25S rRNA), snR9(nucleotide 2339 in 25S rRNA), snR11 (nucleotide 2415 in 25S rRNA), snR36(nucleotide 1185 in 18S rRNA), and snR189(nucleotide 2730 in 25S rRNA). See Balakin et al., Cell, 86:823–834, 1996 for citations; and Ganot et al., Cell, 89:799–809, 1997.

Plasmid construction and site-directed mutagenesis

The wild type SNR8 gene was cloned by PCR amplification of DNA from yeast strain YS602 using primers (5'-CCGGAATCCGATGCCATATTTCTCTGCCTTG-3'; SEQ ID NO:3) and (5'-CGCGGATCCTGGCCGGGTAACAGAAAACTGTC-3'; SEQ ID NO:4). The product was inserted into SmaI-BamHI sites of a CEN plasmid pRS316 (Sikorski et al., Genetics, 122:19–27, 1989) to yield plasmid pJN44. Mutations were generated by a PCR-based method (Chen et al., Biotechniques, 17:657–659, 1994) using pJN44 as the template. The oligonucleotides used for the mutations are: ACA box mutation (AUA to CUA), 5'-TGCGCGAGTGAGCTATCTTTCATTC-3'(SEQ ID NO:5); S1, 5'-GCCCAGAACAGTGTGATGACGCTCATGAGTG-3' (SEQ ID NO:6); I1, 5'-TGCGCGAGTGAGCATATCTTTCATTC-3' (SEQ ID NO:7); D1, 5'-TGCGCGAGTGAATATCTTTCATTC-3' (SEQ ID NO:8); D2' 5'-CAGATCGGTAGCTGGCGAGTGAGATATC-3' (SEQ ID NO:9); and D3, 5'-CCAGATCGGTAGCTGCGAGTGAGATATC-3' (SEQ ID NO:10).

The SNR3 gene was amplified by PCR amplification of total DNA from YS602 cells, using primers: 5'-CCGGAATTCTATAAGGTCGTTACTACCGTTG-3' (SEQ ID NO:11) and 5'-CGCGGATCCTTTGATTGCACCCATACGG-3' (SEQ ID NO:12). The resulting DNA fragment was cloned into plasmid pRS316. A plasmid containing the SNR33 gene was described previously (Balakin et al., Biochemistry, 32:9754–9762, 1993).

Analysis of ψ Modifications

Formation of ψ in rRNA was examined by a primer extension procedure developed by Bakin et al., *Biochemistry*, 32:9754–9762 (1993), resuspended in 50 μl of H$_2$O, and then split into two aliquots which were dried and subsequently treated with or without N-cyclohexyl-N'-β-(4-methylmorpholinium)-ethylcarbodiimide p-tosylate (CMC). Samples were hydrolyzed in 50 mM NaCO$_3$, pH 10.4, for 4 hours, precipitated, dried and dissolved in 20–25 μl of H$_2$O pretreated with diethylpyrocarbonate, 2 μl of each sample were used for primer extension reactions as described in (Balakin et al., *Nucleic Acids Res.* 21:5391–5397, 1993). For each snoRNA tested, 30 of 43 ψ sites in the small and large subunit rRNAs were screened, using a total of 14 primers. The primers were 20–22 nucleotides in length and complementary to rRNA segments 6–50 nucleotides downstream of the 3'-most ψ site.

Computer Analysis of snoRNA Secondary Structures

The computer programs FoldRNA and MFold from the Wisconsin package of the Genetics Computer Group (GCG), version 8, were used in modeling secondary structures. About 20 structures, both optimal and sub-optimal, were obtained for each snoRNA.

Other Embodiments

It is to be understood that, while the invention has been described in conjunction with the detailed description thereof, the foregoing description is intended to illustrate and not limit the scope of the invention. Other aspects, advantages, and modifications of the invention are within the scope of the following claims.

---

We claim:

1. A modified small nucleolar ribonucleic acid (snoRNA) that directs the conversion of a uridine to a pseudouridine in a target nucleic acid that includes first and second flanking regions located on either side of the uridine, the modified snoRNA comprising a ribonucleotide sequence of a box H/ACA snoRNA including (i) a Domain A sequence and (ii) a Domain B or C sequence, wherein the box H/ACA snoRNA ribonucleotide sequence is modified in that the Domain A sequence is replaced by a first recognition sequence complementary to at least three consecutive nucleotides in the first flanking region in the target nucleic acid, and the Domain B or C sequence is replaced by a second recognition sequence complementary to at least three consecutive nucleotides in the second flanking region in the target nucleic acid.

2. The modified snoRNA of claim 1, wherein the first flanking region in the target nucleic acid is located zero, one, or two nucleotides downstream of the uridine.

3. The modified snoRNA of claim 2, wherein the first flanking region in the target nucleic acid is located one nucleotide downstream of the uridine.

4. The modified snoRNA of claim 1, wherein the Domain B sequence is replaced by the second recognition sequence, and the second flanking region in the target nucleic acid is located seven to fourteen nucleotides upstream of the uridine.

5. The modified snoRNA of claim 1, wherein the Domain C sequence is replaced by the second recognition sequence, and the second flanking region in the target nucleic acid is located zero, one, or two nucleotides upstream of the uridine.

6. The modified snoRNA of claim 1, wherein the ACA box of the box H/ACA snoRNA consists of the nucleotides ACA, AUA, or AAA.

7. The modified snoRNA of claim 1, wherein the H box of the box H/ACA snoRNA consists of the nucleotides AGANNA, N being any nucleotide.

8. The modified snoRNA of claim 1, wherein the Domain B sequence is replaced by the second recognition sequence, and the ACA or H box is located at least 14 nucleotides downstream from a first nucleotide in the modified snoRNA that is base-paired with a second nucleotide (i) located on the 5' end of the modified snoRNA and (ii) opposite the uridine when the recognition sequences of the modified snoRNA are hybridized to the flanking regions of the target nucleic acid.

9. The modified snoRNA of claim 8, wherein the ACA or H box is located 15 nucleotides downstream from the first nucleotide.

10. The modified snoRNA of claim 1, wherein the Domain C sequence is replaced by the second recognition sequence, and the ACA or H box is located at least 13 nucleotides downstream from a nucleotide in the modified snoRNA that is opposite the uridine when the recognition sequences of the modified snoRNA are hybridized to the flanking regions of the target nucleic acid.

11. The modified snoRNA of claim 10, wherein the ACA or H box is located 14 nucleotides downstream from the nucleotide.

12. The modified snoRNA of claim 1, wherein the target nucleic acid is ribonucleic acid.

13. A nucleic acid construct comprising a nucleic acid sequence encoding a modified snoRNA of claim 1.

14. A method of directing pseudouridylation, in a yeast cell, of a selected uridine in a target nucleic acid that includes first and second flanking regions located on either side of the uridine, the method comprising:

obtaining a modified snoRNA of claim 1; and contacting the target nucleic acid with the modified snoRNA under conditions sufficient for the first and second recognition sequences to hybridize to the first and second flanking regions in the target nucleic acid, thereby directing the pseudouridylation of the selected uridine.

15. The method of claim 14, wherein the first flanking region in the target nucleic acid is located zero, one, or two nucleotides downstream of the selected uridine.

16. The method of claim 15, wherein the first flanking region in the target nucleic acid is located one nucleotide downstream of the selected uridine.

17. The method of claim 14, wherein the Domain B sequence in the modified snoRNA is replaced by the second recognition sequence, and the second flanking region in the target nucleic acid is located seven to fourteen nucleotides upstream of the selected uridine.

18. The method of claim 14, wherein the Domain C sequence is replaced by the second recognition sequence, and the second flanking region in the target nucleic acid is located zero, one, or two nucleotides upstream of the selected uridine.

19. The method of claim 14, wherein the ACA box of the box H/ACA snoRNA consists of the nucleotides ACA, AUA, or AAA.

20. The method of claim 14, wherein the H box of the box H/ACA snoRNA consists of the nucleotides AGANNA, N being any nucleotide.

21. The method of claim 14, wherein the Domain B sequence is replaced by the second recognition sequence, and the ACA or H box is located at least 14 nucleotides downstream of a first nucleotide in the modified snoRNA that is base-paired with a second nucleotide (i) located on the 5' end of the modified snoRNA and (ii) opposite the uridine, when the recognition sequences of the modified snoRNA are hybridized to the flanking regions of the target nucleic acid.

22. The method of claim 21, wherein the ACA or H box is located 15 nucleotides downstream of the first nucleotide.

23. The method of claim 14, wherein the Domain C sequence is replaced by the second recognition sequence, and the ACA or H box is located at least 13 nucleotides downstream from a nucleotide in the modified snoRNA that is opposite the uridine when the recognition sequences of the modified snoRNA are hybridized to the flanking regions of the target nucleic acid.

24. The method of claim 23, wherein the ACA or H box is located 14 nucleotides downstream from the nucleotide.

25. The method of claim 14, wherein the target nucleic acid is ribonucleic acid.

26. The method of claim 14, wherein the target nucleic acid is in a yeast cell.

27. The method of claim 14, wherein said pseudouridylation occurs in vitro.

28. A modified snoRNA comprising the nucleotide sequence of a naturally occurring box H/ACA snoRNA, wherein at least one ribosomal RNA-complementary sequence of the box H/ACA snoRNA is replaced with a heterologous sequence.

29. The modified snoRNA of claim 28, wherein two ribosomal RNA-complementary sequences of the H/ACA box snoRNA are replaced with first and second heterologous sequences.

30. A nucleic acid construct comprising a nucleic acid sequence encoding a modified snoRNA of claim 28.

31. A method of directing pseudouridylation, in a yeast cell, of a selected uridine in a target nucleic acid, the method comprising:

obtaining a modified snoRNA of claim 28, wherein the heterologous sequence is complementary to a flanking region 3' to the selected uridine in the target nucleic acid; and contacting the target nucleic acid with the modified snoRNA under conditions sufficient for the heterologous sequence to hybridize to the flanking region, thereby directing the pseudouridylation of the selected uridine.

32. A method of directing pseudouridylation, in a yeast cell, of a selected uridine in a target nucleic acid that includes first and second flanking regions located on either side of said selected uridine, the method comprising:

obtaining a modified snoRNA of claim 29, wherein the first and second heterologous sequences are complementary to the first and second flanking regions, respectively; and contacting the target nucleic acid with the modified snoRNA under conditions sufficient for the first and second heterologous sequences to hybridize to the first and second flanking regions, thereby directing the pseudouridylation of the selected uridine.

* * * * *

SEQUENCE LISTING

```
<160> NUMBER OF SEQ ID NOS: 36

<210> SEQ ID NO 1
<211> LENGTH: 20
<212> TYPE: DNA
<213> ORGANISM: Yeast

<400> SEQUENCE: 1
ccatgtcttg aagcttcttc                                                 20

<210> SEQ ID NO 2
<211> LENGTH: 29
<212> TYPE: DNA
<213> ORGANISM: Yeast

<400> SEQUENCE: 2
cgcggatcct gcagcattcc aagccactc                                       29

<210> SEQ ID NO 3
<211> LENGTH: 31
<212> TYPE: DNA
<213> ORGANISM: Yeast

<400> SEQUENCE: 3
ccggaatccg atgccatatt tctctgcctt g                                    31

<210> SEQ ID NO 4
<211> LENGTH: 32
<212> TYPE: DNA
<213> ORGANISM: Yeast

<400> SEQUENCE: 4
cgcggatcct ggccgggtaa cagaaaactg tc                                   32

<210> SEQ ID NO 5
<211> LENGTH: 25
<212> TYPE: DNA
<213> ORGANISM: Yeast

<400> SEQUENCE: 5
tgcgcgagtg agctatcttt cattc                                           25

<210> SEQ ID NO 6
<211> LENGTH: 31
<212> TYPE: DNA
```

```
<213> ORGANISM: Yeast

<400> SEQUENCE: 6
gcccagaaca gtgtgatgac gctcatgagt g                                31

<210> SEQ ID NO 7
<211> LENGTH: 26
<212> TYPE: DNA
<213> ORGANISM: Yeast

<400> SEQUENCE: 7
tgcgcgagtg agcatatctt tcattc                                      26

<210> SEQ ID NO 8
<211> LENGTH: 24
<212> TYPE: DNA
<213> ORGANISM: Yeast

<400> SEQUENCE: 8
tgcgcgagtg aatatctttc attc                                        24

<210> SEQ ID NO 9
<211> LENGTH: 28
<212> TYPE: DNA
<213> ORGANISM: Yeast

<400> SEQUENCE: 9
cagatcggta gctggcgagt gagatatc                                    28

<210> SEQ ID NO 10
<211> LENGTH: 28
<212> TYPE: DNA
<213> ORGANISM: Yeast

<400> SEQUENCE: 10
ccagatcggt agctgcgagt gagatatc                                    28

<210> SEQ ID NO 11
<211> LENGTH: 31
<212> TYPE: DNA
<213> ORGANISM: Yeast

<400> SEQUENCE: 11
ccggaattct ataaggtcgt tactaccgtt g                                31

<210> SEQ ID NO 12
<211> LENGTH: 28
<212> TYPE: DNA
<213> ORGANISM: Yeast

<400> SEQUENCE: 12
cgcggatcct ttgattgcac ccatacgg                                    28

<210> SEQ ID NO 13
<211> LENGTH: 13
<212> TYPE: RNA
<213> ORGANISM: Yeast
<220> FEATURE:
<221> NAME/KEY: misc_feature
<222> LOCATION: (1)...(13)
OTHER INFORMATION: n is pseudouridne

<400> SEQUENCE: 13
cagunuuaug agg                                                    13
```

<210> SEQ ID NO 14
<211> LENGTH: 46
<212> TYPE: RNA
<213> ORGANISM: Yeast

<400> SEQUENCE: 14
acacucauga gcguccucau acugcgguag cugcgcgagu gagaua          46

<210> SEQ ID NO 15
<211> LENGTH: 46
<212> TYPE: RNA
<213> ORGANISM: Yeast

<400> SEQUENCE: 15
acacucauga gcgucaucac acugcgguag cugcgcgagu gagaua          46

<210> SEQ ID NO 16
<211> LENGTH: 16
<212> TYPE: RNA
<213> ORGANISM: Yeast

<400> SEQUENCE: 16
cugcgcgagu gagaua          16

<210> SEQ ID NO 17
<211> LENGTH: 17
<212> TYPE: RNA
<213> ORGANISM: Yeast

<400> SEQUENCE: 17
cugcgcgagu gagcaua          17

<210> SEQ ID NO 18
<211> LENGTH: 15
<212> TYPE: RNA
<213> ORGANISM: Yeast

<400> SEQUENCE: 18
cugcgcgagu gaaua          15

<210> SEQ ID NO 19
<211> LENGTH: 15
<212> TYPE: RNA
<213> ORGANISM: Yeast

<400> SEQUENCE: 19
cuggcgagug agaua          15

<210> SEQ ID NO 20
<211> LENGTH: 14
<212> TYPE: RNA
<213> ORGANISM: Yeast

<400> SEQUENCE: 20
cugcgaguga gaua          14

<210> SEQ ID NO 21
<211> LENGTH: 41
<212> TYPE: RNA
<213> ORGANISM: Yeast
<220> FEATURE:
<221> NAME/KEY: misc_feature
<222> LOCATION: (1)...(41)
<223> OTHER INFORMATION: n is pseudouridine

```
<400> SEQUENCE: 21
aaacggcggg aguaacuaug acncucuuag guagccaaau g                    41

<210> SEQ ID NO 22
<211> LENGTH: 82
<212> TYPE: RNA
<213> ORGANISM: Yeast

<400> SEQUENCE: 22
ccgggucauu uauaagaacu cgaguggauu gcuaguuguu uugauuagcu gaaugagacu  60
cgagugucag aagaugacua ua                                         82

<210> SEQ ID NO 23
<211> LENGTH: 57
<212> TYPE: RNA
<213> ORGANISM: Yeast
<220> FEATURE:
<221> NAME/KEY: misc_feature
<222> LOCATION: (1)...(57)
<223> OTHER INFORMATION: n is pseudouridine

<400> SEQUENCE: 23
aguuucccnc aggauagcag aagcucguau cagunuuaug agguaaagcg aaugauu     57

<210> SEQ ID NO 24
<211> LENGTH: 98
<212> TYPE: RNA
<213> ORGANISM: Yeast

<400> SEQUENCE: 24
acacucauga gcguccucau acguucugg gcgcuucuca caggugcuuc uuuuaguguc   60
ucccauuggc ccagaucggu agcugcgcga gugagaua                        98

<210> SEQ ID NO 25
<211> LENGTH: 42
<212> TYPE: RNA
<213> ORGANISM: Yeast
<220> FEATURE:
<221> NAME/KEY: misc_feature
<222> LOCATION: (1)...(42)
<223> OTHER INFORMATION: n is pseudouridine

<400> SEQUENCE: 25
auucgguaag cguuggauug nucacccacu aauagggaac au                    42

<210> SEQ ID NO 26
<211> LENGTH: 110
<212> TYPE: RNA
<213> ORGANISM: Yeast

<400> SEQUENCE: 26
aaauuuaucg aucuuggug caacagucuu ucgucgucu guuuuuagc agaucuaagg    60 guuuaccuuc gugugcccgg augaggaccg uugcaaggau ugauaauaca           10

<210> SEQ ID NO 27
<211> LENGTH: 40
<212> TYPE: RNA
<213> ORGANISM: Yeast
<220> FEATURE:
<221> NAME/KEY: misc_feature
<222> LOCATION: (1)...(40)
<223> OTHER INFORMATION: n is pseudouridine

<400> SEQUENCE: 27
```

```
aaaguagggg aucgaagaug ancagauacc gucguagucu                      40
```

<210> SEQ ID NO 28
<211> LENGTH: 104
<212> TYPE: RNA
<213> ORGANISM: Yeast

<400> SEQUENCE: 28

```
auuagaaaga uguaucucca gcuguugaua uuagaggggg aagccuuucu cuuucaccuc   60
gccuuuuuaa acaccugaua caguugguca ugauucguuc uaca                   04
```

<210> SEQ ID NO 29
<211> LENGTH: 44
<212> TYPE: RNA
<213> ORGANISM: Yeast
<220> FEATURE:
<221> NAME/KEY: misc_feature
<222> LOCATION: (1)...(44)
<223> OTHER INFORMATION: n is pseudouridine

<400> SEQUENCE: 29

```
auguugacgc aaugugauun cugcccagug cucugaaugu caaa                   44
```

<210> SEQ ID NO 30
<211> LENGTH: 75
<212> TYPE: RNA
<213> ORGANISM: Yeast

<400> SEQUENCE: 30

```
gauagauuga acguugcugg gcgccuggug uugaucauuu cugaaaugag auauugggaa   60
ucagcuguau cuaca                                                   75
```

<210> SEQ ID NO 31
<211> LENGTH: 38
<212> TYPE: RNA
<213> ORGANISM: Yeast
<220> FEATURE:
<221> NAME/KEY: misc_feature
<222> LOCATION: (1)...(38)
<223> OTHER INFORMATION: n is pseudouridine

<400> SEQUENCE: 31

```
cgaaaugacc uugaccuaun cucaaacuuu aaauaugu                          38
```

<210> SEQ ID NO 32
<211> LENGTH: 67
<212> TYPE: RNA
<213> ORGANISM: Yeast

<400> SEQUENCE: 32

```
cuuuuacacc gguuugaguc gguuccuucg uuuucuuagu uggaauugau auagaagugu   60
guggaca                                                            67
```

<210> SEQ ID NO 33
<211> LENGTH: 38
<212> TYPE: RNA
<213> ORGANISM: Yeast
<220> FEATURE:
<221> NAME/KEY: misc_feature
<222> LOCATION: (1)...(38)
<223> OTHER INFORMATION: n is pseudouridine

<400> SEQUENCE: 33

```
uugauucuuc gaugucggcn cuuccuauca uaccgaag                          38
```

```
<210> SEQ ID NO 34
<211> LENGTH: 78
<212> TYPE: RNA
<213> ORGANISM: Yeast

<400> SEQUENCE: 34
uuuggacagg auaggaaguc cgauuucugu guugucucaa acgaggcgau agaauuggga      60
ugucgaagaa agucuaca                                                   78

<210> SEQ ID NO 35
<211> LENGTH: 36
<212> TYPE: RNA
<213> ORGANISM: Yeast
<220> FEATURE:
<221> NAME/KEY: misc_feature
<222> LOCATION: (1)...(36)
<223> OTHER INFORMATION: n is pseudouridine

<400> SEQUENCE: 35
accgucguga gacaggunag uuuuacccua cugaug                               36

<210> SEQ ID NO 36
<211> LENGTH: 92
<212> TYPE: RNA
<213> ORGANISM: Yeast

<400> SEQUENCE: 36
uaauccaucu uuaaaaccau cgccguuaga gguugcuucu gagauuucgg uuaagcgacc      60
caugaaaugg ugaugaccug agguauggaa ca                                   92
```